US00PP23530P3

(12) United States Plant Patent
Bradford

(10) Patent No.: US PP23,530 P3
(45) Date of Patent: Apr. 16, 2013

(54) PEACH TREE NAMED 'JUNE TIME'

(50) Latin Name: *Prunus persica*
Varietal Denomination: June Time

(76) Inventor: Lowell Glen Bradford, Le Grand, CA (US)

( * ) Notice: Subject to any disclaimer, the term of this patent is extended or adjusted under 35 U.S.C. 154(b) by 347 days.

(21) Appl. No.: 12/928,444

(22) Filed: Dec. 13, 2010

(65) Prior Publication Data

US 2012/0151643 P1 Jun. 14, 2012

(51) Int. Cl.
*A01H 5/00* (2006.01)

(52) U.S. Cl. ..... Plt./197

(58) Field of Classification Search ..... Plt./197
See application file for complete search history.

(56) References Cited

U.S. PATENT DOCUMENTS

PP7,070 P 12/1989 Bradford

*Primary Examiner* — June Hwu

(57) ABSTRACT

The present invention relates to a new and distinct variety of peach tree, *Prunus persica,* broadly characterized by a large size, vigorous, hardy, self-fertile, productive and regular bearing tree. The variety blooms during the mid to late season and requires about 600 chilling hours. The fruit matures under the ecological conditions described in mid June, with first picking on Jun. 16, 2010. The fruit is uniformly large in size, acidic in flavor, globose in shape, clingstone in type, firm and non-melting in texture, yellow with red bleeding in flesh color, and mostly dark red in skin color.

1 Drawing Sheet

Botanical classification: *Prunus persica.*
Variety denomination: 'JUNE TIME'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'June Time'.

In the spring of 2003 I gathered open pollinated fruit from various unnamed peach seedlings that were located in our experimental orchard located near Le Grand, Calif., in Merced County (San Joaquin Valley). I removed the seeds from the fruit, stratified them, germinated them, grew them as a group of seedlings on their own root in my greenhouse, and upon reaching dormancy transplanted them to a cultivated area of this experimental orchard with the label 'YP (OP).' During the fruit evaluation season of 2007 I selected the present variety as a single tree from the group of seedlings described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to 'Crown Princess' (U.S. Plant Pat. No. 7,070) peach by producing peaches that are yellow in flesh color, non-melting in texture, and globose in shape, but is distinguished therefrom by requiring less chilling hours, by being more productive, by having reniform instead of globose leaf glands, and by producing fruit that is larger in size, darker red in skin color, that has a sweet instead of bitter kernel, that has a more traditional peach flavor, and that matures about five days later.

SUMMARY OF VARIETY

In summary, the present peach variety is characterized by a large size, vigorous, hardy, self-fertile, productive and regular bearing tree. The variety blooms during the mid to late season and requires about 600 chilling hours. The fruit matures under the ecological conditions described in mid June, with first picking on Jun. 16, 2010. The fruit is uniformly large in size, acidic in flavor, globose in shape, clingstone in type, firm and non-melting in texture, yellow with red bleeding in flesh color, and mostly dark red in skin color.

DRAWING

The accompanying photograph consists of four whole fruits positioned to display the characteristics of the skin color and form, one sliced fruit to reveal the flesh and stone, two insets to reveal buds and a blossom, a tip shoot, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of full shipping ripe on Jun. 25, 2010, on the original tree during its seventh growing season. The blossom and flower descriptions were made the previous blooming season. All major color code designations are by reference to the Inter-Society Color Council, National Bureau of Standards. Common color names are also used occasionally.

It is to be noted that the climatic conditions in 2010 led to delayed fruit ripening for most of the season by approximately ten days. This should be taken into account when comparing to other variety descriptions made referencing different years. However, the relative blooming times and ripening times cited in this application are accurate for 2010, and should remain about the same in future years.

Parentage:

Seed parent: Unknown peach seedling (unpatented).
Pollen parent: Self pollinated.

Tree:

Size: Large, reaching and maintaining a height of 12' [3.66 m.] and a spread of 12' [3.66 m.] after seven growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Pruned to a vase form.
Hardiness: Hardy with respect to central California winters.
Chilling requirement: 600 hours.
Heat tolerance: Observed to perform adequately in typical central California climatic conditions, which typically include extended periods of heat.
Drought tolerance: Variety is developed for commercial orchards and requires regular irrigation.
Production: Very productive, thinning usually necessary.
Fertility: Self-fertile.
Bearing: Regular bearer, with no crop failures observed.
Trunk:
*Size.*—Medium, reaching a maximum diameter of 4½" [114 mm.] after the seventh growing season.
*Texture.*—Shaggy.
*Bark color.*—A Moderate brown [58. m.Br] and Dark grayish brown [62. d.gy.Br] variegation with Light yellowish brown [76. l.yBr] crevices present.
*Lenticels.*—Approximate Number Per Square Inch: 8. Color: Deep orange yellow [69. deep OY]. Average Size: 5/16" [7.9 mm.]. Shape: Eye-shaped, elongated.
Branches:
*Size.*—Diameter of limb is 2¾" [69.9 mm.] measured 12" above the crotch, 2" [50.8 mm.] measured 12" above the first fork.
*Texture.*—Smooth on first and second year wood, increasing roughness with age.
*Color.*—1st Year Wood Topside: Grayish red [19. gy.R]. 1st Year Wood Underside: Brilliant yellow green [116. brill.YG]. 2nd Year Wood: Deep yellowish brown [75. deep yBr]. Older Year Wood: Strong yellowish brown [74. s.yBr] with a Dark yellowish brown [78. d.yBr] variegation.
*Lenticels.*—Number Per Square Inch: About 80 on second year wood. Color: Moderate orange yellow [71. m.OY]. Average Size: 1/16" [1.6 mm.]. Shape: Elongated, rectangular.
Leaves:
*Size.*—Medium. Average Length: 6" [152.4 mm.]. Average Width: 1¾" [44.5 mm.].
*Arrangement.*—Alternate.
*Thickness.*—Medium.
*Form.*—Elliptical.
*Apex.*—Acuminate.
*Base.*—Acute with an average angle of 90 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ⅜" [9.5 mm.]. Average Thickness: 3/32" [2.4 mm.]. Color: Very yellow green [115. v.YG].
*Stipules.*—Number: 2 per leaf, up to 6 per growing tip. Average Length: ⅜" [9.5 mm.]. Color: Brilliant yellow green [116. brill.YG] becoming Strong reddish brown [40. s.rBr] with age.
*Glands.*—Number: Mostly 2 per leaf. Position: Alternately positioned on petiole and the rest on base of blade. Size: Small. Form: Reniform. Color: Strong greenish yellow [99. s.gY] becoming Moderate reddish brown [43. m.rBr] in the center with age.
*Leaf buds.*—Pointed, medium.
Flower buds:
*Hardiness.*—Hardy, with respect to central California winters.
*Diameter.*—Typically ⅜" [9.5 mm.] 1 week before bloom.
*Length.*—Typically ¾" [19.1 mm.] 1 week before bloom.
*Form.*—Not appressed.
*Surface.*—Pubescent.
*Tip color.*—Moderate purplish pink [250. m.pPk].
Flowers: Perfect, complete, perigynous, usually a single pistil, typically thirty or more stamens, five sepal and petal locations alternately positioned.
*Type.*—Showy, large.
*Average flower diameter.*—1 15/16" [49.2 mm.].
*Number of petals.*—Usually five, extra petal fragments commonly occur, double blossoms rarely observed.
*Petal shape.*—Circular to oval.
*Petal margin.*—Entire, somewhat wavy, occasional notches.
*Average petal diameter.*—¾" [19.1 mm.].
*Average petal length.*—¾" [19.1 mm.].
*Petal apex.*—Rounded.
*Petal Base.*—Rounded to somewhat truncate.
*Petal color.*—Light pink [4. l.Pk] throughout on both sides, Strong pink [2. s.Pk] toward the base on a few.
*Anther color.*—Dark red [16. d.R] over a Light yellow [86. l.Y] center at bloom onset.
*Stigma color.*—Pale yellow green [121. p.YG].
*Sepal color.*—Dark purplish red [259. d.pR].
*Sepal length.*—¼" [6.4 mm.].
*Sepal width.*—3/16" [4.8 mm.].
*Average pistil length.*—13/16" [20.6 mm.].
*Average stamen length.*—⅝" [15.9 mm.].
*Fragrance.*—Moderate.
*Blooming period.*—Medium to late, about five days before 'Crown Princess' (U.S. Plant Pat. No. 7,070) peach.
*Onset of bloom.*—One percent on Feb. 23, 2010.
*Date of full bloom.*—Mar. 4, 2010.
*Duration of bloom.*—One to two weeks, dependent on ambient temperature.
*Number per cluster.*—1 to 3 with single flowers most common.

FRUIT

Maturity when described: Firm ripe, Jun. 25, 2010.
Date of first picking: Jun. 16, 2010.
Date of last picking: Jun. 26, 2010.

Size: Uniform, large.
*Average diameter axially.*—2¾" [69.9 mm.].
*Average diameter across suture plane.*—3" [76.2 mm.].
*Average diameter across cheek plane.*—3⅛" [79.4 mm.]
*Typical weight.*—8.2 ounces [232.47 grams].
Form: Uniform, globose, symmetrical.
*Longitudinal section form.*—Elliptical, compressed axially.
*Axial view.*—Round.
Suture: Extends from the base to just past the pistil point.
*Near the base.*—A sharp groove.
*Along the side.*—A shallow trough.
*Near the apex.*—A shallow groove.
Ventral surface: Rounded, lipped toward the apex on both sides.
Lips: Equal.
Cavity: Flaring, elongated in the suture plane, suture showing on both sides, Brilliant yellow [83. brill.Y] stem markings typical.
*Depth.*—¾" [19.1 mm.].
*Breadth.*—1⅜" [34.9 mm.].
Base: Truncate, somewhat cordate if viewed parallel to suture.
Apex: Rounded to slightly truncate, slightly cordate if viewed parallel to the suture.
Pistil point: Apical, negligible in length, depressed within the suture.
Stem: Medium.
*Average length.*—7/16" [11.1 mm.].
*Average width.*—3/16" [4.8 mm.].
Skin:
*Thickness.*—Medium.
*Surface.*—Pubescent.
*Tenacity.*—Tenacious to the flesh.
*Astringency.*—Moderate.
*Tendency to crack.*—None observed in wet season.
*Color.*—Dark grayish red [20. d.gy.R] over a Deep red [13. deep R] background with Very yellow [82. v.Y] areas near the stem cavity on some if sun protected.
*Down.*—Moderate, very short, does not roll up when rubbed.
Flesh:
*Color.*—Very yellow [82. v.Y] with heavy Very reddish orange [34. v.rO] bleeding toward the skin.
*Surface of pit cavity.*—Pale yellow [89. p.Y] broken fibers when twisted from stone.
*Amygdalin.*—Moderate.
*Juice.*—Moderate, rich.
*Texture.*—Firm, tough, nonmelting.
*Fibers.*—Abundant, tough.
*Ripens.*—Fairly evenly, earlier toward the apex.
*Flavor.*—Traditional peach flavor, acidic and sweet, typically 12 brix.
*Aroma.*—Moderate.
*Eating quality.*—Very good.

STONE

Type: Clingstone.
Form: Oval.
Hilum: Narrow.
Base: Rounded, slightly obligue.
Apex: Acute to acuminate with an average tip angle of 60 degrees.
Sides: Equal.
Surface: Irregularly furrowed and ridged toward the apex, pitted from the base to the center.
Ridges: Jagged.
External color: Light yellowish brown [76. l.yBr].
Pit wall color when cracked: Light yellowish brown [76. l.yBr].
Cavity surface color: Light yellowish brown [76. l.yBr].
Average pit wall thickness: ¼" [6.4 mm.].
Average width: 1" [25.4 mm.].
Average length: 1½" [38.1 mm.].
Average breadth: ¾" [19.1 mm.].
Tendency to split: Very slight.
Kernel:
*Form.*—Oval.
*Skin Color.*—Pale yellow [89. p.Y] when first removed.
*Pellicle color.*—Dark orange yellow [72. d.OY].
*Vein color.*—Dark orange yellow [72. d.OY].
*Taste.*—Sweet.
*Viable.*—Yes.
*Average width.*—½" [12.7 mm.].
*Average Length.*—¾" [19.1 mm.].
*Amygdalin.*—Scant.

Use

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Crown Princess' (U.S. Plant Pat. No. 7,070) peach by producing peaches that are yellow in flesh color, non-melting in texture, and globose in shape, but is distinguished therefrom by requiring less chilling hours, by being more productive, by having reniform instead of globose leaf glands, and by producing fruit that is larger in size, darker red in skin color, that has a sweet instead of bitter kernel, that has a more traditional peach flavor, and that matures about five days later.

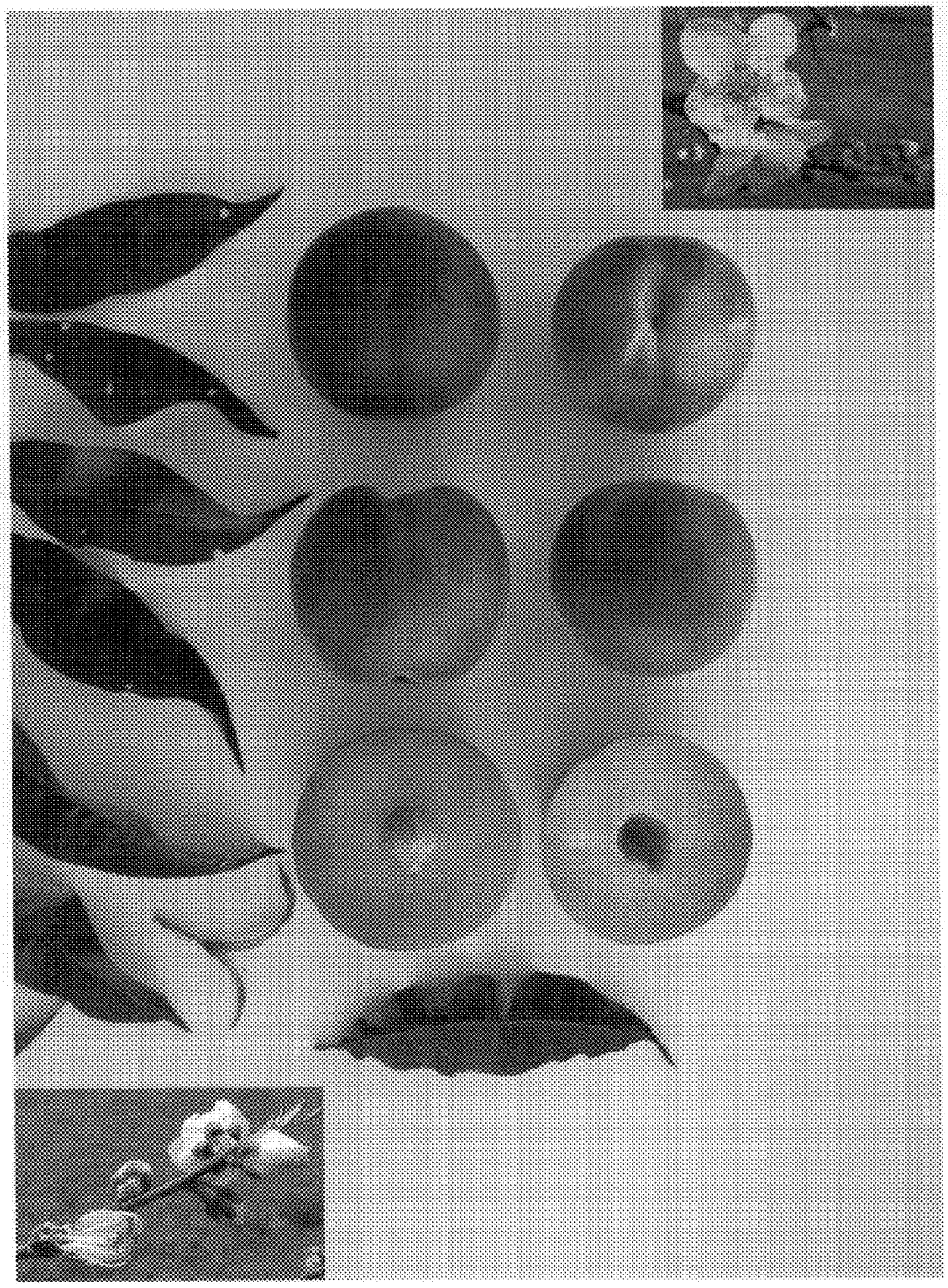

* * * * *